Figure 1:
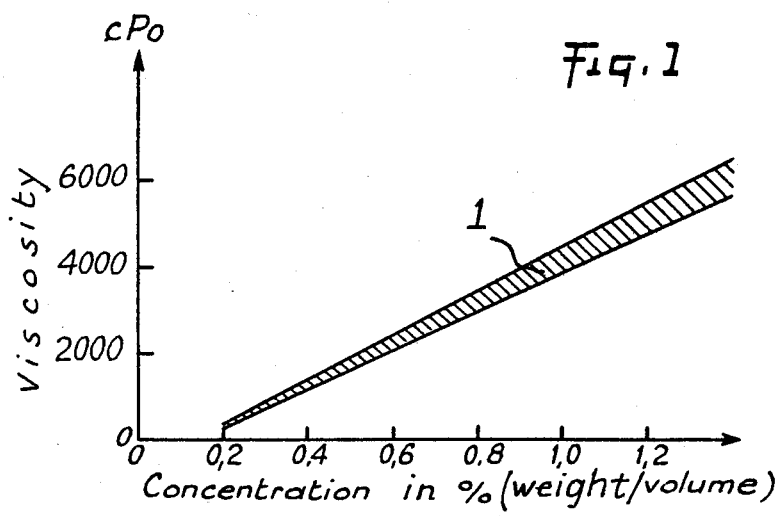

United States Patent

Duc

[11] 4,396,611
[45] Aug. 2, 1983

[54] GLYCOSYLGLUCANS AND APPLICATION IN GASTROENTEROLOGY

[75] Inventor: Amaury N. C. Duc, Brecy, France

[73] Assignee: Laboratoires Debat, Paris, France

[21] Appl. No.: 288,377

[22] Filed: Jul. 30, 1981

[30] Foreign Application Priority Data

Aug. 5, 1980 [EP] European Pat. Off. .......... 80 401154

[51] Int. Cl.$^3$ ..................... A61K 31/715; C08B 37/00
[52] U.S. Cl. .................................... 424/180; 536/1.1; 536/123
[58] Field of Search ..................... 424/181, 180; 536/1

[56] References Cited

U.S. PATENT DOCUMENTS

| | | | |
|---|---|---|---|
| 3,301,848 | 1/1967 | Halleck | 536/1 |
| 3,436,311 | 4/1969 | Ferguson et al. | 536/1 |
| 3,507,290 | 4/1970 | Halleck | 536/1 |
| 3,659,025 | 4/1972 | Halleck | 536/1 |
| 3,754,925 | 8/1973 | Kimura et al. | 536/1 |
| 3,900,462 | 8/1975 | Komatani et al. | 536/1 |
| 3,987,166 | 10/1976 | Komatsu et al. | 536/1 |
| 4,237,266 | 12/1980 | Sugiura et al. | 536/1 |

FOREIGN PATENT DOCUMENTS 2406477 10/1978 France .

*Primary Examiner*—Johnnie R. Brown

*Attorney, Agent, or Firm*—Schwartz, Jeffery, Schwaab, Mack, Blumenthal & Koch

[57] ABSTRACT

The present invention relates to a medicament selected from the group consisting of glycosylglucans corresponding to the general formula

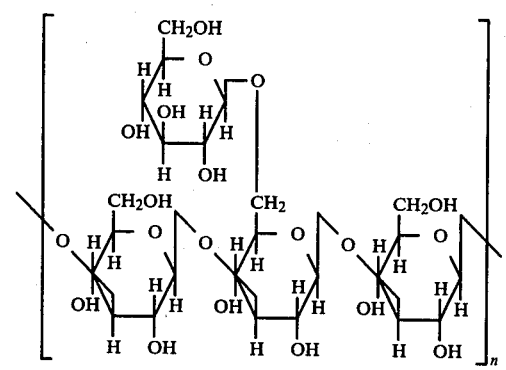

(where n is an integer) and the molecular weight of which is between about 130,000 and 1,200,000 and preferably between about 500,000 and about 600,000. This medicament is particularly useful in gastroenterology and in particular in the treatment of disorders of the colon; it is administered by the oral route in association with a physiologically acceptable excipient.

9 Claims, 3 Drawing Figures

GLYCOSYLGLUCANS AND APPLICATION IN GASTROENTEROLOGY

The present invention relates to a new medicament belonging to the family of glycosylglucans corresponding to the formula I given below. The invention also relates to the application of this medicament in gastroenterology, particularly in the treatment of disorders of the colon, in the form of a therapeutic composition.

The use of poly-1,3-β-glucosides having a linear polysaccharide chain in opthalmic compositions is already known from U.S. Pat. No. 3,415,929, said compositions being administered by the local route and including a vehicle for prolonging the action of the active ocular ingredients.

The use of cross-linked polysaccharides, having a linear poly-1,3-glucopyranoside linear chain laterally cross-linked by 1,6-glucopyranose residues, in cosmetics for setting hair, as well as, in association with emollients and water for the care of the skin is known from U.S. Pat. Nos. 3,507,290 and 3,659,025.

Furthermore, cross-linked polysaccharides of the type having a linear poly-1,3-glucopyranoside linear chain laterally cross-linked by 1,6-glucopyranose residues, which are water soluble and have a molecular weight greater than or equal to $1.5 \times 10^6$ (and especially equal to $2 \times 10^6$) are known in therapy as anti-tumor substances from U.S. Pat. Nos. 4,237,266 and 3,987,166.

Surprisingly, it has been found that certain of the polysaccharides of U.S. Pat. Nos. 3,507,290 and 3,659,025, belonging to the family of glycosylglucans of the formula I given below (which, in contrast to the polysaccharides of U.S. Pat. No. 4,237,266 and U.S. Pat. No. 3,987,166, have a molecular weight between 130,000 and 1,200,000 and swell in water) are used in therapy by the oral route, especially in gastroenterology and in particular as agents for improving intestinal transit for the treatment of disorders of the colon.

The new medicament according to the invention is characterised in that it is selected from the group consisting of glycosylglucans corresponding to the general formula:

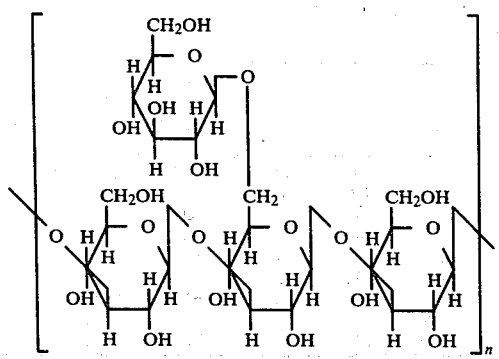

(where n is an integer) and the molecular weight of which is between about 130,000 and about 1,200,000, preferably between about 500,000 and about 600,000.

The glycosylglucans according to the invention are polymers having as a repeating unit a chain of three 1,3 glucopyranosyl groups, the central group being substituted by a 1,6-glucopyranosyl group. The expanded formula I may be schematically represented by the condensed formula:

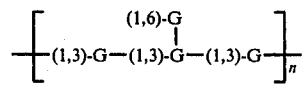

(where n is as defined above and G represents a glucopyranosyl residue $C_6H_{10}O_5$).

The polymers according to the invention have a mean molecular weight between about 130,000 and 1,200,000, that is to say the invention includes products whose degree of polymerisation is approximately between about 200 and about 1850.

The most interesting of these polymers, so far as gastro-enterologic properties and industrial preparation, particularly by fermentation, are concerned are those whose molecular weight is between 500,000 and 600,000, that is to say products of the formula I where n is an integer between about 770 and about 925. Among these latter polymers the preferred glycosylglucan according to the invention is that which has a degree of polymerisation n which is on the order of about 800.

Figure 2:
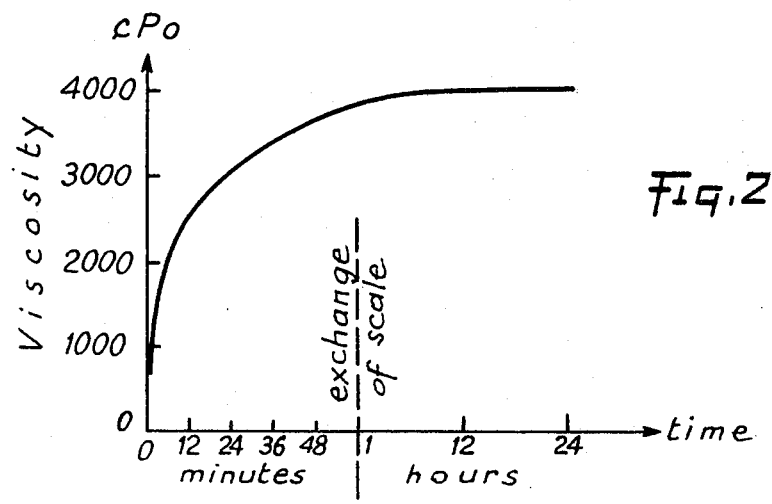

The glycosylglucans of formula I according to the invention are non-ionic homopolysaccharides which have physico-chemical properties which are characterised as follows:

A—VISCOSITY: The viscosity of sols increases as a function of the concentration (c.f. FIG. 1). For a given concentration, the viscosity increases as a function of hydration time so as to arrive at a maximum value at about 12–24 hours (c.f. FIG. 2). The viscosity is practically independent of pH and is stable between pH 0 and pH 12.5, all things being equal otherwise. The viscosity is not influenced by variations in temperature between 15° C. and 90° C.

B—INSENSITIVITY TO ELECTROLYTES: The glycosylglucans according to the invention are compatible with the majority of acids, bases and salts over a very large pH range (pH 0 to pH 12.5). No salt, not even the chromic ion, affects the pronounced crosslinking.

C—SWELLING POWER: The glycosylglucans of formula I have a good swelling ability both in water and body fluids (serum, plasma).

Figure 3:
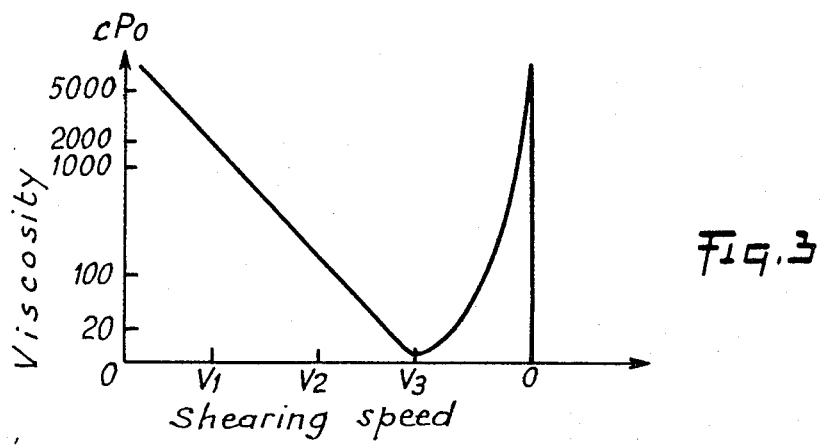

D—RHEOLOGY: The sols have pseudoplastic rheological properties which are more pronounced than those of other known colloids particularly in the field of gastroenterology. The psuedoplasticity is expressed by a high threshold of flow below which the fluid remains immobile, and by an instantaneous reduction of viscosity as soon as there is movement or agitation. This phenomenon is reversible (c.f. FIG. 3). It results in rheological properties (high viscosity at rest, fluiditity increasing as a function of movement) so that the glycosylglucans according to the invention are self-lubricating.

The preferred product (the polymer of formula I having a degree of polymerisation n on the order of 800) which has the code number DU-80 possesses the following specific properties:

1°—The variation of its rotatory power in alkaline medium (NaOH 0.13 N-0.01 N) has been studied (on a FICA SPECTROPOL 1B apparatus) at 25° C., under nitrogen, at a concentration of 0.72 g/l in water. Under these conditions there is obtained $$a_D^{25° C.} = 100°/\text{ml/g}$$

2°—The variation of its viscosity (expressed in cPo; bearing in mind that 1 centipoise corresponds to $10^{-3}$ pascal-seconds) as a function of the concentration in water (expressed in % weight/volume) has been determined with dispersant, at 20° C. (BROOKFIELD LVF apparatus, needle No. 3, 30 revs/min) and is represented by the hatched area in FIG. 1.

3°—The variation of its viscosity (expressed in cPo) as a function of hydration time has been determined without dispersant and at a concentration of 1% weight/volume in water (BROOKFIELD LVF apparatus, needle No. 3, 30 revs/min) and is represented by the curve of FIG. 2 (for convenience, this curve is traced with a change of scale in the abscissa: time in seconds to 60 minutes, then time in hours from 1 hour). It will be observed that in the time 12-24 h. the viscosity of DU-80, at a concentration of 1% (weight/volume) in water, reaches the maximum value of 4,000 cPo.

4°—In order to appreciate its psuedoplasticity, the variation of viscosity (expressed in cPo) as a function of shearing speed has been studied by means of a BROOKFIELD LVF viscometer (needle No. 3, at 6, 12, 30, and 60 revs/min). The curve of FIG. 3 (which was registered on a cylinder) shows the development of viscosity of a DU-80 sol (concentration on the order of 1.4% weight/volume in water) which is agitated starting from rest (V=0) with increasing shearing speed (0 < V-1 < V2 < V3) until the speed V3 is obtained.

5°—Its absorbent power is very important. DU-80 may absorb up to 60 times its weight of water without flowing.

The glycosylglucans of formula I may be prepared according to a method known per se. They may be obtained by fermentation according to the procedure described in the aforementioned U.S. Pat. Nos. 3,507,290 and 3,659,025.

They are used in therapy, especially in gastroenterology. They improve intestinal transit and they are very interesting in the treatment of disorders of the colon (intestinal atony, intestinal sluggishness, constipation).

Besides their property of improving intestinal transit, they have other advantageous effects in therapy related to their role as swelling agents: in particular, they may act as anoretic agents (by giving a feeling of fullness when they line the wall of the stomach) and as sequestering agents for bile acids.

According to the invention there is provided a therapeutic composition which is useful in gastroenterology and particularly in the treatment of disorders of the colon, characterised in that it comprises, in association with a physiologically acceptable excipient, at least one glycosylglucan of formula I having a molecular weight between about 130,000 and about 1,200,000, and preferably between about 500,000 and 600,000. The glycosylglucan of greatest interest has a degree of polymerisation n on the order of 800.

For oral administration the glycosylglucans according to the invention may be prepared in the form of capsules, sachets or gels. Administration to adults is advantageously carried out in the form of capsules which may include, if necessary, a flowing agent or a lubricating agent, such as magnesium stearate, to augment the self-lubricating properties of the glycosylglucan. Administration to children is advantageously carried out in the form of gels, including aromatisation agents and preserving agents, as the case may be. The results of toxicological and pharmacological tests which have been undertaken with the glycosylglucans according to the invention are summarised hereinafter.

1°—Toxicity

The LD-O (maximum non-toxic dose) per os in the male rat is greater than 5 g/kg.

Moreover, chronic toxicity tests, per os in the dog and the rat, have provided evidence that the glycosylglucans according to the invention, at a daily dose of 2 g/kg for 90 days, did not result in any mortalities.

2°—Tolerance

Non-irritability tests for the eyes and dermal and intestinal tolerance tests have shown that the glycosylglucans according to the invention do not have a deleterious effect on mucous membranes.

3°—Action on intestinal transit

The action on intestinal transit has been studied according to the technique of LOEWE and FAURE, Arch. Exp. Path. Pharm. 107, 271 (1925). Female Sprague-Dawley rats having a mean weight of 110 g, were divided into lots each containing 10 animals ((1 lot according to dose and product to be tested and 1 lot as a control receiving only water) and were put on a 24 hour fast before the administration per os of the product in water (at a volume of 2 ml per 100 g body weight). Thirty minutes after the administration of the products to be tested, a suspension of charcoal was administered (10 g of vegetable charcoal in 100 ml of water). 20 minutes after the administration of the charcoal, the animals are sacrificed and bled. The small intestine is dissected by cutting at the level of the pylorus and the caecum. The total length (L) of the small intestine and the length (l) traversed by the charcoal is measured. The relationship $$\frac{l \times 100}{L},$$

is determined, which expresses the percentage length traversed by the charcoal and the percentage increase in intestinal transit compared with the control sample.

The results obtained, which are recorded in table I, show that DU-80 is significantly more active than the reference product, sterculia gum.

TABLE I

| Product | Dose mg/kg | L (cm) | l (cm) | $\frac{l \times 100}{L}$ | Increase in transit with respect to the control lot |
|---|---|---|---|---|---|
| Control | — | 103.5 | 53.5 | 51.7 | Base 100 |
| Sterculia | 100 | 104 | 65 | 63 | 122% |
| Sterculia | 1000 | 102 | 64 | 62 | 120% |
| DU-80 | 12.5 | 105 | 60 | 58 | 112% |
| DU-80 | 25 | 104 | 64 | 62 | 120% |
| DU-80 | 50 | 106 | 62 | 59 | 114% |
| DU-80 | 75 | 105 | 63 | 60 | 116% |
| DU-80 | 100 | 104.5 | 70.5 | 67.5 | 131% |
| DU-80 | 1000 | 105 | 74 | 71 | 138% |

4°—Resistance to pancreatic juice

In vitro tests carried out with pig pancreatin [which includes several enzymes (amylase, trypsin and other proteases, lipases and ribonuclease)] has allowed verification that the glycosylglucans of formula I according to the invention and, in particular, DU-80, are not destroyed by amylase and pig pancreatin. In fact, after hydrolysis for 22 hours the quantity of glucose freed has proved to be nil.

I claim:

1. A method of treating intestinal transit disorders comprising orally administering an effective intestinal transit improving amount of a glycosylglucan corresponding to the formula:

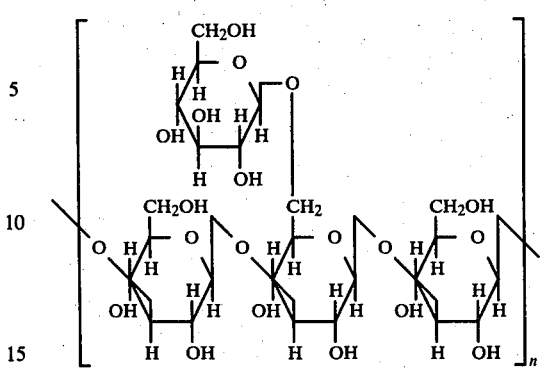

wherein n represents an integer greater than about 200.

2. A method according to claim 1 wherein said glycosylglucan is administered in the form of a capsule.

3. A method according to claim 1 wherein said glycosylglucan is administered in the form of a gel.

4. A method according to claim 1 wherein said glycosylglucan has a mean molecular weight from about 130,000 to about 1,200,000.

5. A method according to claim 1 wherein n represents an integer from about 200 to about 1850.

6. A method according to claim 1 wherein the mean molecular weight of said glycosylglucan is from about 500,000 to about 600,000.

7. A method according to claim 1 wherein n is about 800.

8. A method according to claim 1 wherein the specific rotation of said glycosylglucan in an alkaline medium at 25° C. under nitrogen and at a concentration of 0.72 g/l is $\alpha_D^{25°\ C.} = 100°/\text{ml/g}$.

9. A method according to claim 1 wherein said glycosylglucan is in the form of an aqueous sol, and said sol is viscous when at rest and fluid when agitated.

* * * * *